(12) United States Patent  (10) Patent No.: US 7,752,920 B2
Blumenkranz et al.  (45) Date of Patent: Jul. 13, 2010

(54) MODULAR FORCE SENSOR

(75) Inventors: Stephen J. Blumenkranz, Redwood City, CA (US); David Q. Larkin, Menlo Park, CA (US); Rajesh Kumar, Nasirpur (IN)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 851 days.

(21) Appl. No.: 11/553,303

(22) Filed: Oct. 26, 2006

(65) Prior Publication Data

US 2007/0151391 A1  Jul. 5, 2007

Related U.S. Application Data

(60) Provisional application No. 60/755,157, filed on Dec. 30, 2005.

(51) Int. Cl.
G01D 7/00 (2006.01)
(52) U.S. Cl. .............................. 73/862.045; 73/862.041
(58) Field of Classification Search ................................
73/862.041–862.046
See application file for complete search history.

(56) References Cited

U.S. PATENT DOCUMENTS

| | | | |
|---|---|---|---|
| 3,878,713 A * | 4/1975 | Mole | 73/147 |
| 3,929,009 A * | 12/1975 | Lutz et al. | 73/862.338 |
| 4,343,198 A * | 8/1982 | Jendrzejczyk | 73/862.042 |
| 4,369,663 A | 1/1983 | Venturello et al. | |
| 4,906,907 A | 3/1990 | Tsuchihashi et al. | |
| 5,513,536 A | 5/1996 | Reger et al. | |
| 5,631,973 A | 5/1997 | Green | |
| 5,807,377 A | 9/1998 | Madhani et al. | |
| 6,331,181 B1 | 12/2001 | Tierney et al. | |
| 6,371,952 B1 | 4/2002 | Madhani et al. | |
| 6,435,030 B1 * | 8/2002 | Gysling et al. | 73/587 |
| 6,470,205 B2 | 10/2002 | Bosselmann et al. | |
| 6,491,701 B2 | 12/2002 | Tierney et al. | |
| 6,676,684 B1 | 1/2004 | Morley et al. | |
| 6,770,081 B1 | 8/2004 | Cooper et al. | |
| 6,783,524 B2 | 8/2004 | Anderson et al. | |
| 6,817,974 B2 | 11/2004 | Cooper et al. | |
| 6,866,671 B2 | 3/2005 | Tierney et al. | |
| 6,879,880 B2 | 4/2005 | Nomlin et al. | |

(Continued)

FOREIGN PATENT DOCUMENTS

DE  3405168 A1  8/1985

(Continued)

OTHER PUBLICATIONS

PCT/US06/62000 International Search Report and Written Opinion of the International Searching Authority, mailed Nov. 12, 2007, 10 pages.

(Continued)

*Primary Examiner*—Max Noori

(57) ABSTRACT

A modular force sensor apparatus, method, and system are provided to improve force and torque sensing and feedback to the surgeon performing a telerobotic surgery. In one embodiment, a modular force sensor includes a tube portion including a plurality of strain gauges, a proximal tube portion for operably coupling to a shaft of a surgical instrument that may be operably coupled to a manipulator arm of a robotic surgical system, and a distal tube portion for proximally coupling to a wrist joint coupled to an end portion.

29 Claims, 8 Drawing Sheets

U.S. PATENT DOCUMENTS

| | | | |
|---|---|---|---|
| 6,902,560 | B1 | 6/2005 | Morley et al. |
| 6,936,042 | B2 | 8/2005 | Wallace et al. |
| 7,000,478 | B1* | 2/2006 | Zwollo et al. ................. 73/708 |
| 7,578,219 | B2* | 8/2009 | Wu ............................. 81/165 |
| 2005/0200324 | A1 | 9/2005 | Guthart et al. |
| 2008/0065111 | A1* | 3/2008 | Blumenkranz et al. ...... 606/130 |
| 2009/0157092 | A1* | 6/2009 | Blumenkranz et al. ...... 606/130 |
| 2009/0192522 | A1* | 7/2009 | Blumenkranz ............. 606/130 |
| 2009/0248038 | A1* | 10/2009 | Blumenkranz et al. ...... 606/130 |

FOREIGN PATENT DOCUMENTS

| | | |
|---|---|---|
| EP | 0177919 A | 4/1986 |
| FR | 2693397 A | 1/1994 |
| FR | 2693397 A1 | 1/1994 |
| WO | WO 00/35366 A | 6/2000 |
| WO | WO 2005/122916 A | 12/2005 |

OTHER PUBLICATIONS

Vertut, Jean and Coeffet, Philippe Coiffet; " Robot Technology; vol. 3A Teleoperation and Robotics Evolution and Development"; 1986; Prentice-Hall, Inc; Englewood Cliffs, N.J.

Cepolina, F. and R.C. Michelini, "Review of robotic fixtures for minimally invasive surgery," International Journal of Medical Robotics and Computer Assisted Surgery, 2004, vol. 1, Issue 1, pp. 43-63.

U.S. Appl. No. 08/517,053, filed Aug. 21, 1995, Green.

U.S. Appl. No. 11/314,040, filed Dec. 20, 2005, Joseph Orban.

U.S. Appl. No. 60/752,755, filed Dec. 20, 2005, Devengenzo et al.

U.S. Appl. No. 60,755,108, filed Dec. 30, 2005, Blumenkranz et al.

U.S. Appl. No. 60/755,157, filed Dec. 30, 2005, Larkin et al.

U.S. Appl. No. 11/537,241, filed Sep. 29, 2006, Blumenkranz et al.

F Cepolina, R C Michelini, Review of robotic fixtures for minimally invasive surgery, 2004 Robotic Publications Ltd., Int J Medical Robotics and Computer Assisted Surgery 2004; (1):43-63.

Ulrich Seibold and Gerd Hirzinger, A-Axis Force/Torque Sensor Design for Haptic Feedback in Minimally Invasive Robotic Surgery, Institute for Robotics and Mechatronics, German Aerospace Center (DLR), Oberpfaffenhofen, Germany, 6 pages, 2003.

* cited by examiner

MODULAR FORCE SENSOR

CROSS-REFERENCE TO RELATED APPLICATIONS AND PATENTS

This application claims priority to and the benefit of U.S. Provisional Application 60/755,157, filed Dec. 30, 2005, the full disclosure of which (including all references incorporated by reference therein) is incorporated by reference herein for all purposes.

This application is related to U.S. Provisional Application No. 60/755,108 filed Dec. 30, 2005, U.S. patent application Ser. No. 11/537,241 filed Sep. 29, 2006, U.S. patent application Ser. No. 11/093,372 filed Mar. 30, 2005 (US20050200324 A1, published Sep. 15, 2005), and U.S. Pat. Nos. 6,936,042, 6,902,560, 6,879,880, 6,866,671, 6,817,974, 6,783,524, 6,676,684, 6,371,952, 6,331,181, and 5,807,377, the full disclosures of which (including all references incorporated by reference therein) are incorporated by reference herein for all purposes.

TECHNICAL FIELD

The present invention relates generally to surgical robot systems and, more particularly, to an improved system, apparatus, and method for sensing forces applied to a surgical instrument.

BACKGROUND

In robotically-assisted surgery, the surgeon typically operates a master controller to control the motion of surgical instruments at the surgical site from a location that may be remote from the patient (e.g., across the operating room, in a different room or a completely different building from the patient). The master controller usually includes one or more hand input devices, such as handheld wrist gimbals, joysticks, exoskeletal gloves, handpieces or the like, which are operatively coupled to the surgical instruments through a controller with servo motors for articulating the instruments' position and orientation at the surgical site. The servo motors are typically part of an electromechanical device or surgical manipulator arm ("the slave") that includes a plurality of joints, linkages, etc., that are connected together to support and control the surgical instruments that have been introduced directly into an open surgical site or through trocar sleeves inserted through incisions into a body cavity, such as the patient's abdomen. Depending on the surgical procedure, there are available a variety of surgical instruments, such as tissue graspers, needle drivers, electrosurgical cautery probes, etc., to perform various functions for the surgeon, e.g., retracting tissue, holding or driving a needle, suturing, grasping a blood vessel, or dissecting, cauterizing or coagulating tissue. A surgeon may employ a large number of different surgical instruments/tools during a procedure.

This new method of performing telerobotic surgery through remote manipulation has created many new challenges. One such challenge is providing the surgeon with the ability to accurately "feel" the tissue that is being manipulated by the surgical instrument via the robotic manipulator. The surgeon must rely on visual indications of the forces applied by the instruments or sutures. It is desirable to sense the forces and torques applied to the tip of the instrument, such as an end effector (e.g., jaws, grasper, blades, etc.) of robotic endoscopic surgical instruments, in order to feed the forces and torques back to the surgeon user through the system hand controls or by other means such as visual display or audible tone. One device for this purpose from the laboratory of G. Hirzinger at DLR is described in "Review of Fixtures for Low-Invasiveness Surgery" by F. Cepolina and R. C. Michelini, *Int'l Journal of Medical Robotics and Computer Assisted Surgery*, Vol. 1, Issue 1, page 58, the contents of which are incorporated by reference herein for all purposes. However, that design disadvantageously places a force sensor distal to (or outboard of) the wrist joints, thus requiring wires or optic fibers to be routed through the flexing wrist joint and also requiring the yaw and grip axes to be on separate pivot axes.

Another problem has been fitting and positioning the necessary wires for mechanical actuation of end effectors in as small a space as possible as relatively small instruments are typically desirable for performing surgery.

What is needed, therefore, are improved telerobotic systems and methods for remotely controlling surgical instruments at a surgical site on a patient. In particular, these systems and methods should be configured to provide accurate feedback of forces and torques to the surgeon to improve user awareness and control of the instruments.

SUMMARY

The present invention provides an apparatus, system, and method for improving force and torque feedback to and sensing by the surgeon performing a robotic surgery. In one embodiment, a modular force sensor includes a tube portion including a plurality of strain gauges, a proximal tube portion for operably coupling to a shaft of a surgical instrument that may be operably coupled to a manipulator arm of a robotic surgical system, and a distal tube portion for proximally coupling to a wrist joint coupled to an end portion.

Groups of axially oriented strain gauges are positioned on or near a distal end of an instrument shaft proximal to (or inboard of) a moveable wrist of a robotic surgical instrument via a modular apparatus to sense forces and torques at the distal tip of the instrument without errors due to changes in the configuration of the tip (such as with a moveable wrist) or steady state temperature variations.

Advantageously, the present invention improves the sensing and feedback of forces and/or torques to the surgeon and substantially eliminates the problem of passing delicate wires through the flexible wrist joint of the instrument. A force sensor apparatus may be manufactured, tested, and calibrated as a separate modular component and brought together with other components in the conventional instrument assembly process. In addition, it is possible to choose a material for the sensor structural member different from the material of the instrument shaft whose design considerations may compromise the mechanical properties required for the sensor.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

Figure 1A:
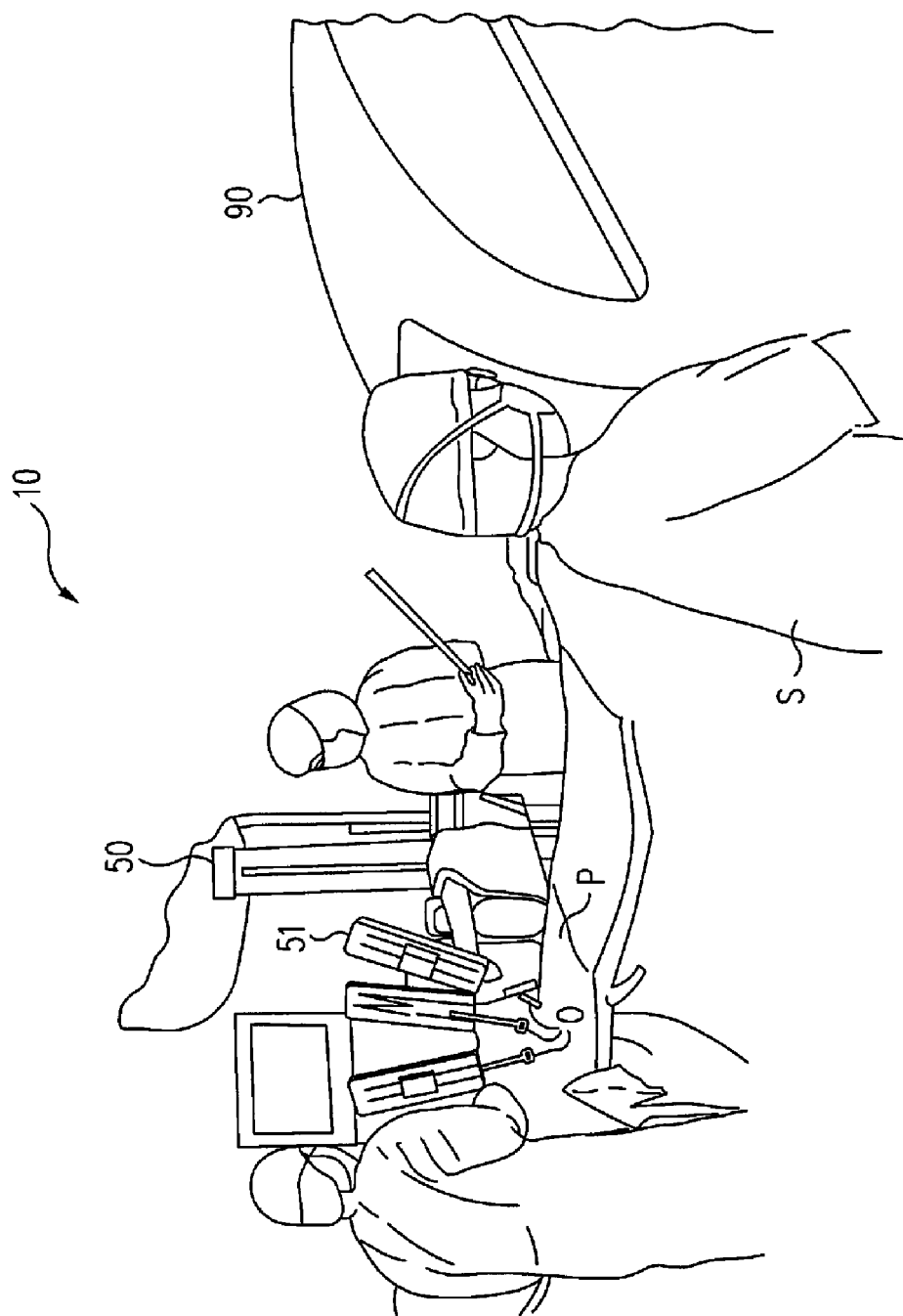
FIG. 1A is a perspective view of a robotic surgical system and method in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a multi-component system, apparatus, and method for sensing forces applied to tissue while performing robotically-assisted surgical procedures on a patient, particularly including open surgical procedures, neurosurgical procedures, such as stereotaxy, and endoscopic procedures, such as laparoscopy, arthroscopy, thoracoscopy and the like. The apparatus and method of the present invention are particularly useful as part of a telerobotic surgical system that allows the surgeon to manipulate the surgical instruments through a servomechanism from a remote location from the patient. To that end, the manipulator apparatus or slave of the present invention will usually be driven by a kinematically-equivalent master having six or more degrees of freedom (e.g., 3 degrees of freedom for position and 3 degrees of freedom for orientation) to form a telepresence system with force reflection. A description of a suitable slave-master system can be found in U.S. patent application Ser. No. 08/517,053, filed Aug. 21, 1995, the complete disclosure of which is incorporated herein by reference for all purposes.

Figure 1B:
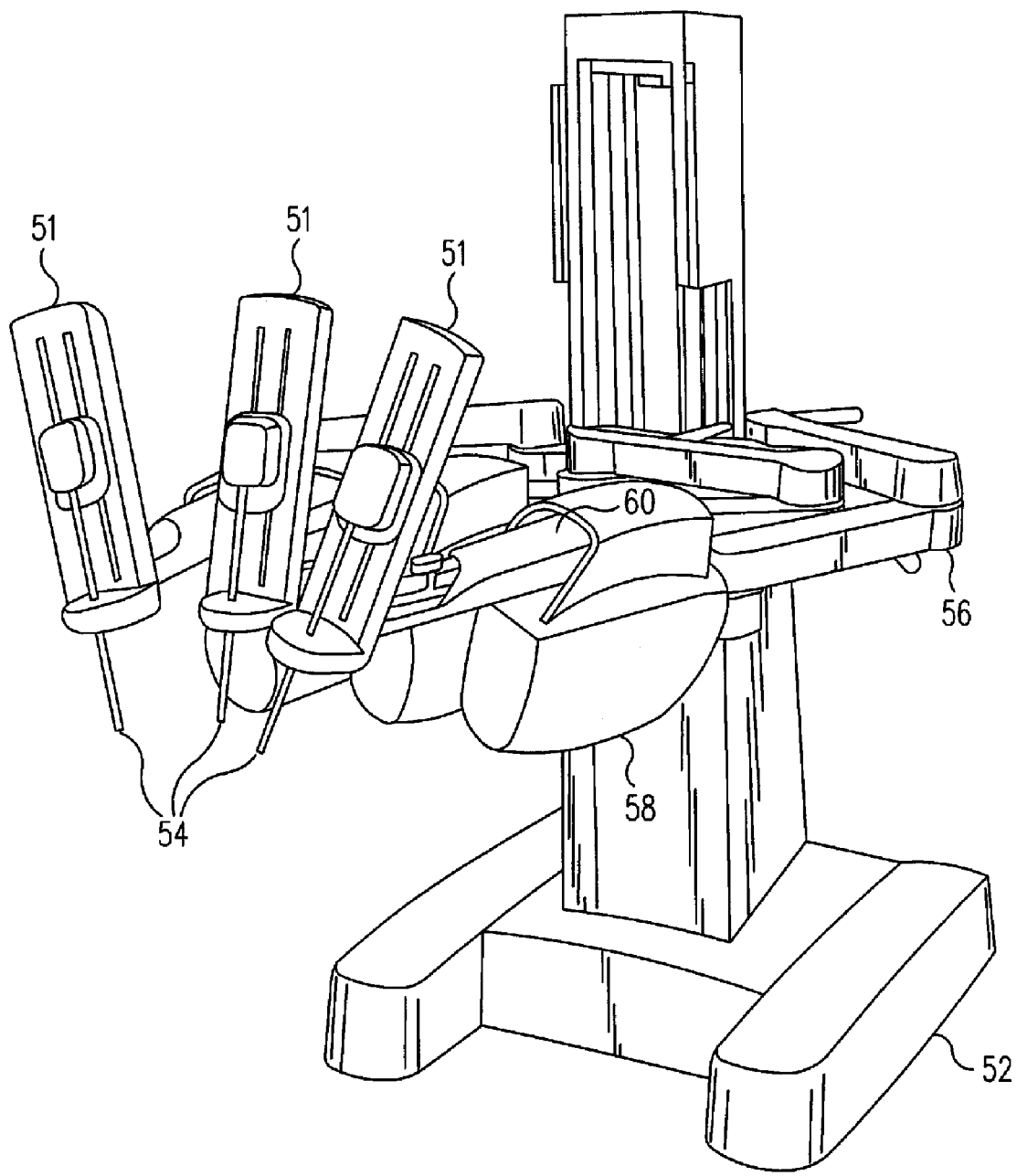
FIG. 1B is a perspective view of a robotic surgical arm cart system of the robotic surgical system in FIG. 1A in accordance with an embodiment of the present invention.
Figure 1C:
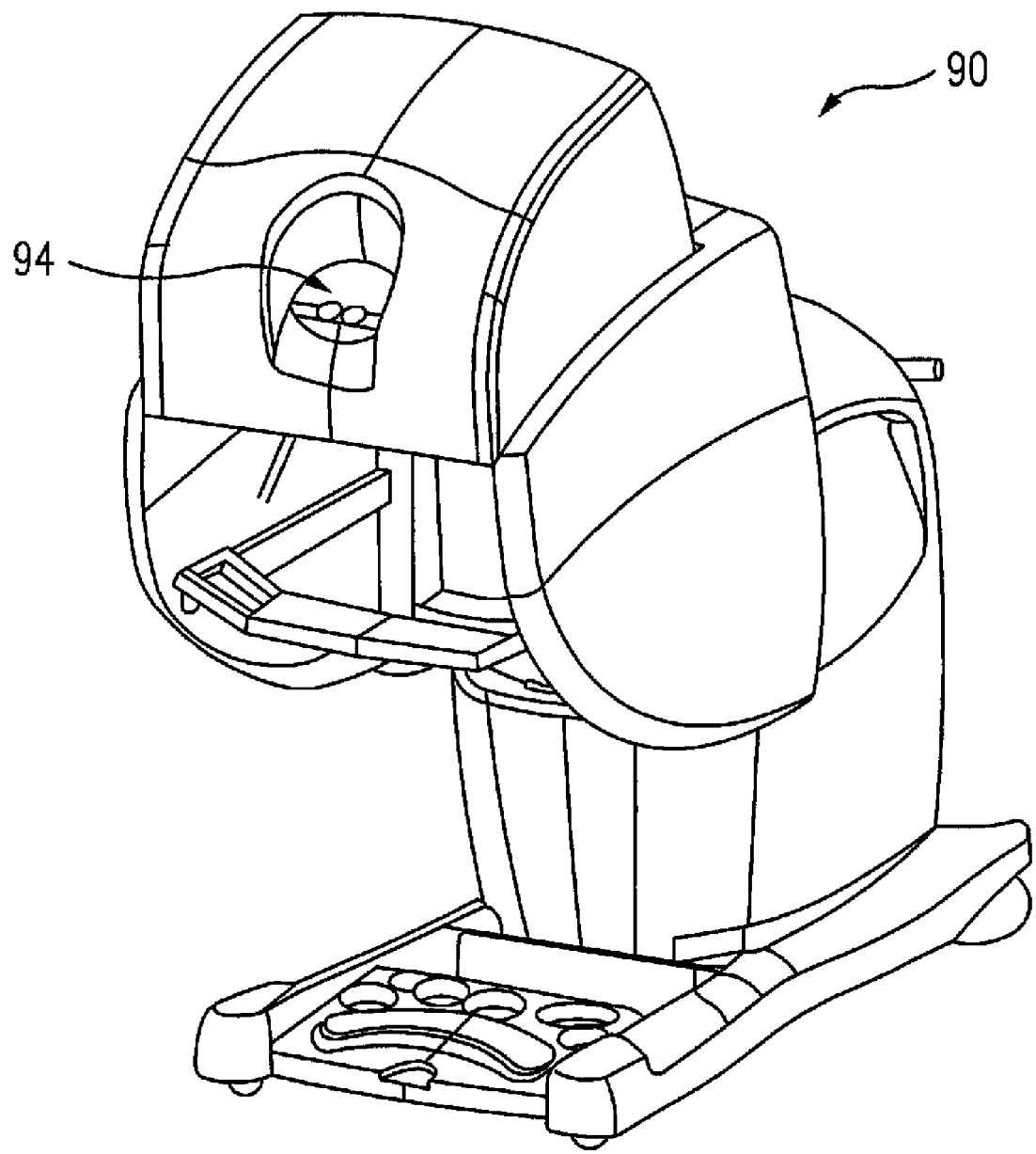
FIG. 1C is a front perspective view of a master console of the robotic surgical system in FIG. 1A in accordance with an embodiment of the present invention.

Referring to the drawings in detail, wherein like numerals indicate like elements, a robotic surgical system 10 is illustrated according to an embodiment of the present invention. As shown in FIGS. 1A through 1C, robotic system 10 generally includes one or more surgical manipulator assemblies 51 mounted to or near an operating table O, and a master control assembly located at a surgeon's console 90 for allowing the surgeon S to view the surgical site and to control the manipulator assemblies 51. The system 10 will also include one or more viewing scope assemblies and a plurality of surgical instrument assemblies 54 adapted for being removably coupled to the manipulator assemblies 51 (discussed in more detail below). Robotic system 10 usually includes at least two manipulator assemblies 51 and preferably three manipulator assemblies 51. The exact number of manipulator assemblies 51 will depend on the surgical procedure and the space constraints within the operating room among other factors. As discussed in detail below, one of the assemblies 51 will typically operate a viewing scope assembly (e.g., in endoscopic procedures) for viewing the surgical site, while the other manipulator assemblies 51 operate surgical instruments 54 for performing various procedures on the patient P.

The control assembly may be located at a surgeon's console 90 which is usually located in the same room as operating table O so that the surgeon may speak to his/her assistant(s) and directly monitor the operating procedure. However, it should be understood that the surgeon S can be located in a different room or a completely different building from the patient P. The master control assembly generally includes a support, a monitor for displaying an image of the surgical site to the surgeon S, and one or more master(s) for controlling manipulator assemblies 51. Master(s) may include a variety of input devices, such as hand-held wrist gimbals, joysticks, gloves, trigger-guns, hand-operated controllers, voice recognition devices or the like. Preferably, master(s) will be provided with the same degrees of freedom as the associated surgical instrument assemblies 54 to provide the surgeon with telepresence, the perception that the surgeon is immediately adjacent to and immersed in the surgical site, and intuitiveness, the perception that the master(s) are integral with the instruments 54 so that the surgeon has a strong sense of directly and intuitively controlling instruments 54 as if they are part of his hands. Position, force, and tactile feedback sensors (not shown) may also be employed on instrument assemblies 54 to transmit position, force, and tactile sensations from the surgical instrument back to the surgeon's hands as he/she operates the telerobotic system. One suitable system and method for providing telepresence to the operator is described in U.S. patent application Ser. No. 08/517,053, filed Aug. 21, 1995, which has previously been incorporated herein by reference.

The monitor 94 will be suitably coupled to the viewing scope assembly such that an image of the surgical site is provided adjacent the surgeon's hands on surgeon console. Preferably, monitor 94 will display an image on a display that is oriented so that the surgeon feels that he or she is actually looking directly down onto the operating site. To that end, an image of the surgical instruments 54 appears to be located substantially where the operator's hands are located even though the observation points (i.e., the endoscope or viewing camera) may not be from the point of view of the image. In addition, the real-time image is preferably transformed into a stereo image such that the operator can manipulate the end effector and the hand control as if viewing the workspace in substantially true presence. By true presence, it is meant that the presentation of an image is a true stereo image simulating the viewpoint of an operator that is physically manipulating the surgical instruments 54. Thus, a controller (not shown) transforms the coordinates of the surgical instruments 54 to a perceived position so that the stereo image is the image that one would see if the camera or endoscope was located directly behind the surgical instruments 54. A suitable coordinate transformation system for providing this virtual image is described in U.S. patent application Ser. No. 08/239,086, filed May 5, 1994, now U.S. Pat. No. 5,631,973, the complete disclosure of which is incorporated herein by reference for all purposes.

A servo control is provided for transferring the mechanical motion of masters to manipulator assemblies 51. The servo control may be separate from, or integral with the console 90. The servo control will usually provide force and torque feedback from the surgical instruments 54 to the hand-operated masters. In addition, the servo control may include a safety monitoring controller (not shown) to safely halt system operation or at least inhibit all robot motion in response to recognized undesirable conditions (e.g., exertion of excessive force on the patient, mismatched encoder readings, etc.). The servo control preferably has a servo bandwidth with a 3 dB cut off frequency of at least 10 hz so that the system can quickly and accurately respond to the rapid hand motions used by the surgeon and yet to filter out undesirable surgeon hand tremors. To operate effectively with this system, manipulator assemblies 51 have a relatively low inertia, and the drive motors have relatively low ratio gear or pulley couplings. Any suitable conventional or specialized servo control may be used in the practice of the present invention, with those incorporating force and torque feedback being particularly preferred for telepresence operation of the system.

Figure 2:
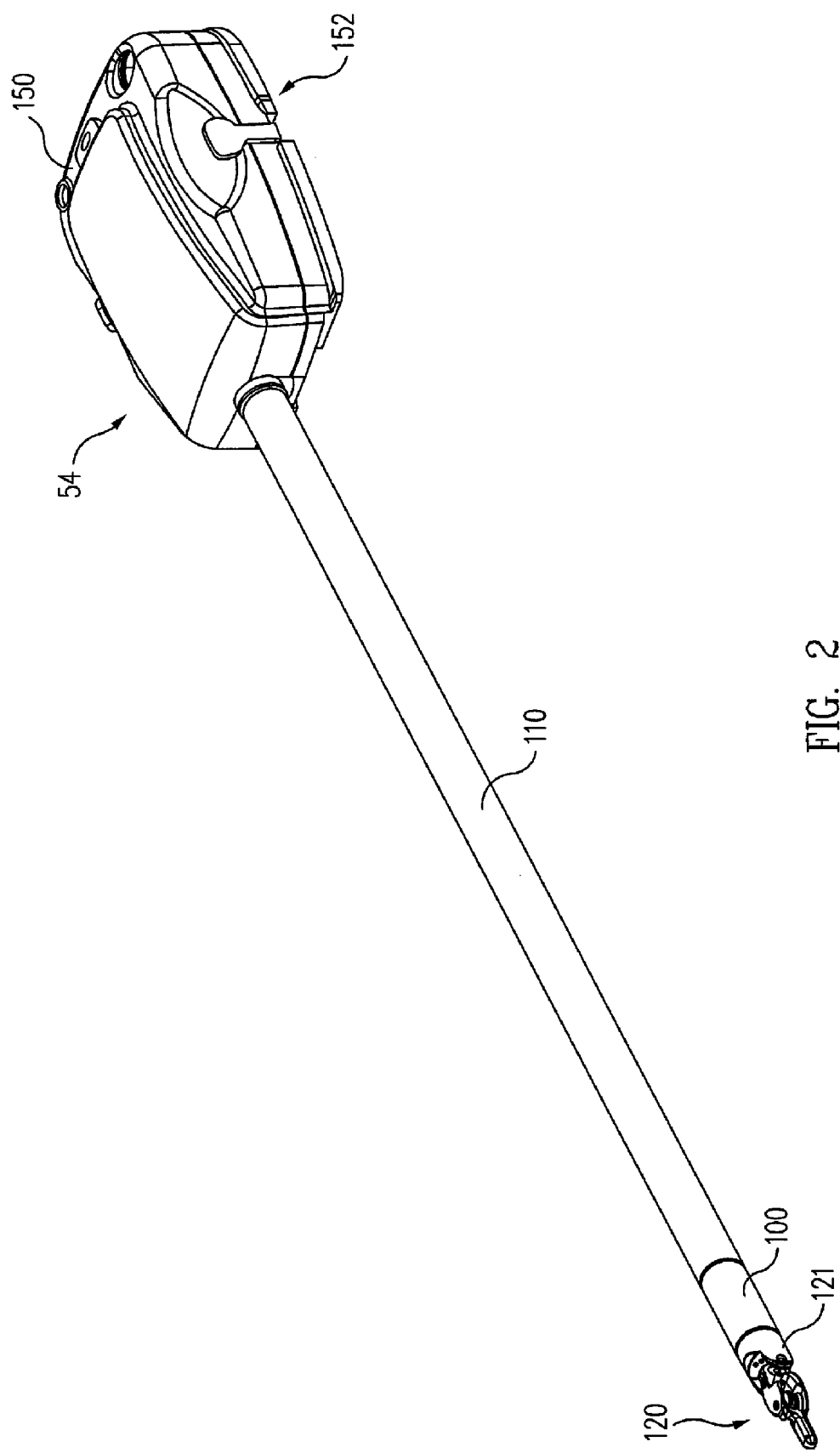
FIG. 2 is a perspective view of a surgical instrument including a modular force sensor apparatus operably coupled proximal (or inboard) to a wrist joint in accordance with an embodiment of the present invention.

Referring to FIG. 2, a perspective view is shown of a surgical instrument 54 including a modular force sensor apparatus 100 operably coupled to a distal end of a rigid shaft 110 and proximal to a wrist joint 121 in accordance with an embodiment of the present invention. An end portion 120, such as a surgical end effector, is coupled to force sensor apparatus 100 via the wrist joint 121. A housing 150 is operably coupled to a proximal end of the rigid shaft 110 and includes an interface 152 which mechanically and electrically couples instrument 54 to the manipulator 51.

Figure 3A:
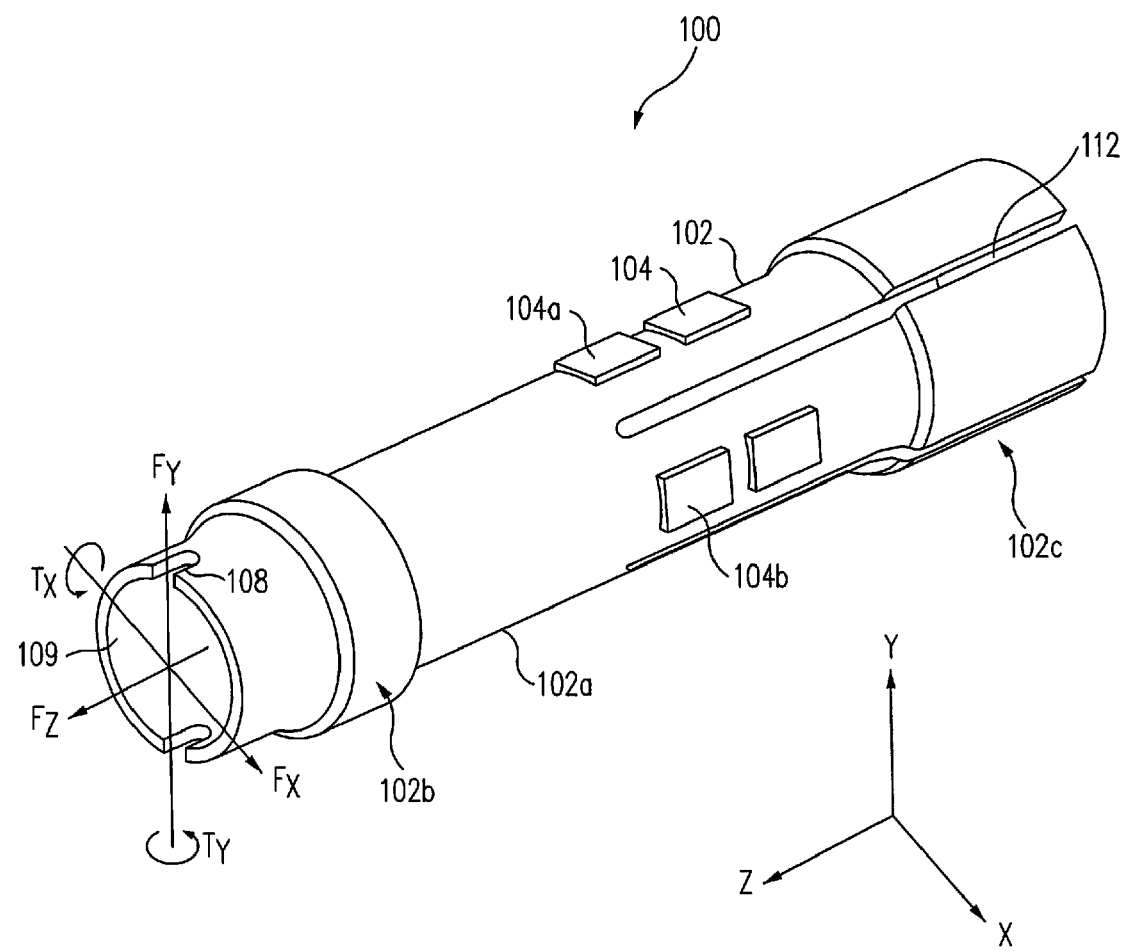
FIG. 3A is a perspective view of a modular force sensor apparatus in accordance with an embodiment of the present invention.
Figure 3B:
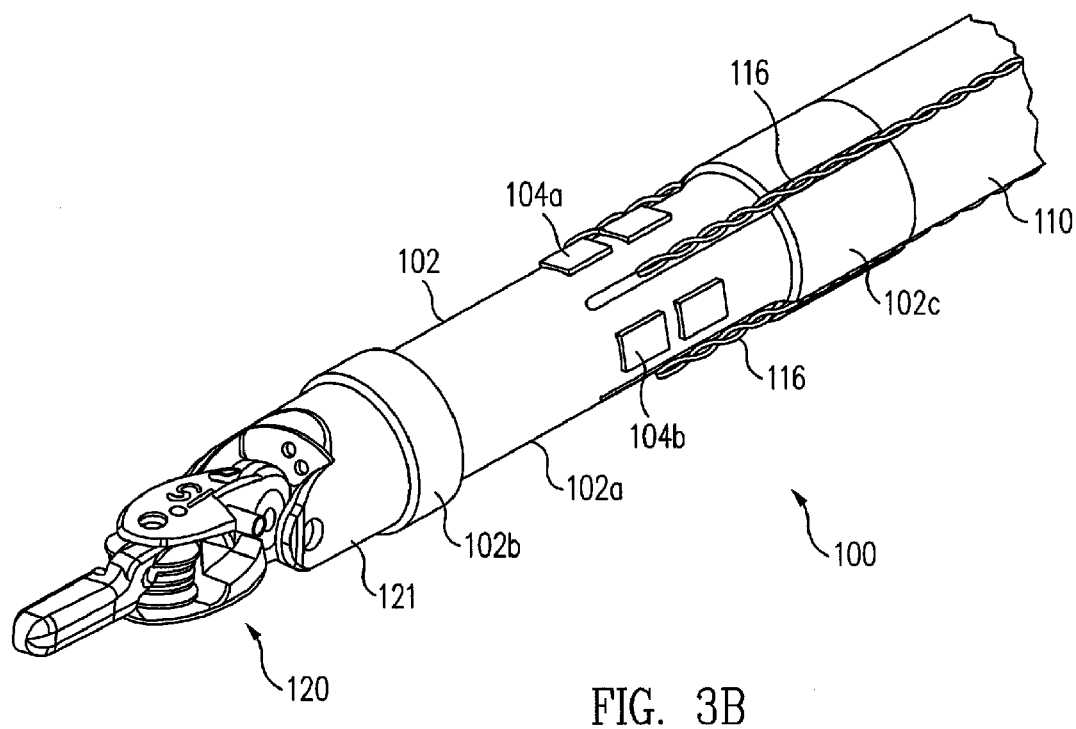
FIG. 3B illustrates the modular force sensor of FIG. 3A operably coupled to a shaft and end portion of a surgical instrument in accordance with an embodiment of the present invention.
Figure 3C:
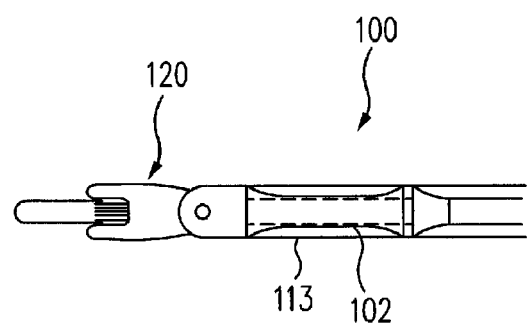
FIG. 3C illustrates the modular force sensor of FIG. 3A with a protective cover over a portion of the modular force sensor in accordance with an embodiment of the present invention.

Referring now to FIGS. 3A-3C in conjunction with FIGS. 1A-1C and 2, an improved apparatus, system, and method for sensing and feedback of forces and/or torques to the surgeon will be described in accordance with an embodiment of the present invention. FIG. 3A shows a perspective view of modular force sensor apparatus 100 including in one embodiment a tube 102 including a number (e.g., 3, 4, 6, or 8) of strain gauges 104 (e.g., 104a and 104b) mounted to a surface of tube 102 and oriented axially (parallel to the lengthwise axis z of the tube). FIG. 3B shows the modular force sensor apparatus 100 of FIG. 3A operably coupled to a shaft 110 and end portion 120 of a surgical instrument in accordance with an embodiment of the present invention. FIG. 3C shows a cross-section view of modular force sensor apparatus 100 including a cover or sleeve 113 over tube 102.

In accordance with an embodiment of the present invention, force sensor apparatus 100 is a separately manufacturable module adapted for incorporation as part of the shaft 110 of laparoscopic surgical instrument 54 at a prescribed distance from the tip where there may be an articulated wrist with specialized jaws, cutting devices, or other end portion 120. In one example, tube 102 may be made of a sufficiently strong material and may be spool shaped, including end portions 102b, 102c with a depressed portion 102a therebetween. Strain gauges 104 may be mounted on the surface of depressed portion 102a. Proximal tube portion 102c operably couples to the shaft 110 of surgical instrument 54 and distal tube portion 102b operably couples to a wrist joint 121. In one example, the diameter of the completed force sensor apparatus matches the diameter of the instrument shaft, thus allowing the entire assembly of the instrument (including the coupled force sensor apparatus) to pass through a cannula or a seal without added friction or snagging.

Force sensor apparatus 100 includes a through passage 109 for end portion actuation cables or rods. End features 108 of end portion 102b insure secure mounting and angular alignment to the main instrument shaft and wrist/jaw/other end portion sub-assembly of the instrument. Wire leads or optic fibers 116 (e.g., shielded twisted pairs, coax, or fiber) from the strain gauges 104 may be inlaid into grooves 112 in proximal tube portion 102c of tube 102 and matching grooves in the shaft 110 of the surgical instrument 54. The wire leads or optic fibers 116 may then be embedded in an adhesive potting compound such as epoxy.

In one embodiment, as illustrated in FIG. 3C, cover 113 is positioned over and encapsulates the mounted strain gauges 104 and other circuit elements on the surface of the tube 102, thereby providing mechanical protection of the sensors. In one example, cover 113 is a mechanically protective woven sleeve potted on depressed portion 102a and is comprised of a woven resin impregnated fiberglass or metal braid electrical shielding.

As disclosed in U.S. Provisional Application No. 60/755,108, filed Dec. 30, 2005, the contents of which have been previously incorporated by reference, strain gauges 104 may be spaced in a ring at intervals around the circumference of the tube 102 (e.g., 3 gauges at 120 degrees or 4 gauges at 90 degrees). The signals from the sensors are combined arithmetically in various sums and differences to obtain measures of three perpendicular forces (e.g., $F_x$, $F_y$, and $F_z$) exerted upon the instrument tip and the torques about the two axes perpendicular to the shaft axis (i.e., axes x and y). In accordance with the present invention, the measurement of the forces is made independent of the orientation and effective lever arm length of an articulated wrist mechanism at the distal end of the instrument when two sets or rings of gauges are utilized. Forces exerted against end portion 120 are detected by the force sensing elements, which may be operably coupled to the servo control via an interrogator or a processor for notifying the surgeon of these forces (e.g., via master(s)). It is understood that by adding a second ring of similarly oriented gauges (e.g., two sets of 3 gauges or two sets of 4 gauges) at a different axial position on the tube, additional applied torque information (e.g., $T_x$ and $T_y$) and elimination of dependence of the force data on instrument wrist length, orientation, and resulting jaw distance, may be obtained.

In one example, various strain gauges may be used, including but not limited to conventional foil type resistance gauges, semiconductor gauges, optic fiber type gauges using Bragg grating or Fabry-Perot technology, or others, such as strain sensing surface acoustic wave (SAW) devices. Optic fiber Bragg grating (FBG) gauges may be advantageous in that two sensing elements may be located along one fiber at a known separation, thereby only requiring the provision of four fibers along the instrument shaft.

Both fiber technologies require an interrogator unit that decodes the optically encoded strain information into electrical signals compatible with the computer control hardware of the robotic surgical system. A processor may then be used to calculate forces according to the signals from the strain gauges/sensors.

Additionally, there may be co-mounted unstrained gauges or Poisson strained gauges oriented in the circumferential direction adjacent to each axial gauge and incorporated in the bridge completion circuits to eliminate temperature effects. The strain gauge bridge circuits are completed in a manner to give the best signal for bending loads due to the lateral forces ($F_x$ and $F_y$) exerted on the instrument tip jaws.

For resistive foil or semiconductor strain gauges, active components such as bare die op-amps and passive components such as secondary resistors or capacitors may be attached adjacent to the strain gauges connected by bond wires or optic fibers or thick film circuit traces in the manner of hybrid circuits to amplify, filter, and/or modulate the gauge output signals to reject noise sources. Such components are not needed for fiber optic gauges.

Surgical instrument 54 to which force sensor apparatus 100 couples may include a circumferentially coiled insulated flex circuit style service loop of parallel conductive traces at the proximal end of the instrument shaft 110 permitting the substantially free rotation of the instrument shaft while conducting the input gauge excitation power and output gauge signals to stationary housing 150 of the instrument 54.

Housing 150 operably interfaces with a robotic manipulator arm 51, in one embodiment via a sterile adaptor interface 152. Applicable housings, sterile adaptor interfaces, and manipulator arms are disclosed in U.S. patent application Ser. No. 11/314,040 and U.S. Provisional Application No. 60/752,755, both filed on Dec. 20, 2005, the full disclosures of which (including all references incorporated by reference therein) are incorporated by reference herein for all purposes. Applicable shafts, end portions, housings, sterile adaptors, and manipulator arms are available from Intuitive Surgical Inc. of Sunnyvale, Calif.

In a preferred configuration, end portion 120 has a range of motion that includes pitch and yaw motion, rotation about the z-axis, and actuation of an end effector, via cables through shaft 110 and housing 150 that transfers motion and electrical signals from the manipulator arm 51. Movement of end portion 120 along the x, y, and z axes may be provided by the manipulator arm 51. Embodiments of drive assemblies, arms, forearm assemblies, adaptors, and other applicable parts are described for example in U.S. Pat. Nos. 6,331,181, 6,491,701, and 6,770,081, the full disclosures of which (including disclosures incorporated by reference therein) are incorporated herein by reference for all purposes.

It is noted that various surgical instruments may be improved in accordance with the present invention, including but not limited to tools with and without end effectors, such as jaws, scissors, graspers, needle holders, micro-dissectors, staple appliers, tackers, suction irrigation tools, clip appliers, cutting blades, irrigators, catheters, and suction orifices. Alternatively, the surgical instrument may comprise an electrosurgical probe for ablating, resecting, cutting or coagulating tissue. Such surgical instruments are commercially available from Intuitive Surgical, Inc. of Sunnyvale, Calif.

For the methods and apparatus mentioned above, it may be advantageous to use a calibration process in which combinations of forces and torques are applied to the instrument tip serially, simultaneously, or in combinations while correction factors and offsets are determined to apply to the theoretical equations for combining the gauge outputs to obtain $F_x$, $F_y$, $F_z$, $T_x$, and $T_y$. This calibration may be done either by directly calculating the correction factors and offsets or by a learning system such as a neural network embedded in the calibration fixture or in the instrument itself. In any calibration method, the calibration data may be programmed into an integrated circuit embedded in the instrument so that the surgical system using the individual instrument can correctly identify and apply its correction factors and offsets while the instrument is in use.

Advantageously, force sensor apparatus 100 of the present invention is adaptable to the size and shape constraints of robotic endoscopic surgical instruments and is suitable for a variety of instruments. Accordingly, end portions 102b, 102c may be formed into various applicable shapes and sizes. Furthermore, force sensor apparatus 100 may be manufactured, tested, and calibrated as a separate modular component and brought together with other components in the conventional instrument assembly process. Also, the sensor may be a slip on module with suitable electrical contacts that mate with contacts on the instrument shaft permitting a higher value sensor to be used with lower cost instruments of limited cycle life. In addition, the sensor structural member 102 may be comprised of an advantageous material, which may be a different material than the instrument shaft 110 whose design considerations may compromise the properties required for the sensor.

Referring now to FIGS. 4A through 4D, a modular force sensor apparatus 200 is illustrated in accordance with another embodiment of the present invention. The descriptions of substantially similar parts or elements as those described above with respect to FIGS. 1-3 are applicable in this embodiment with respect to FIGS. 4A-4D, although redundant descriptions will be omitted.

Figure 4A:
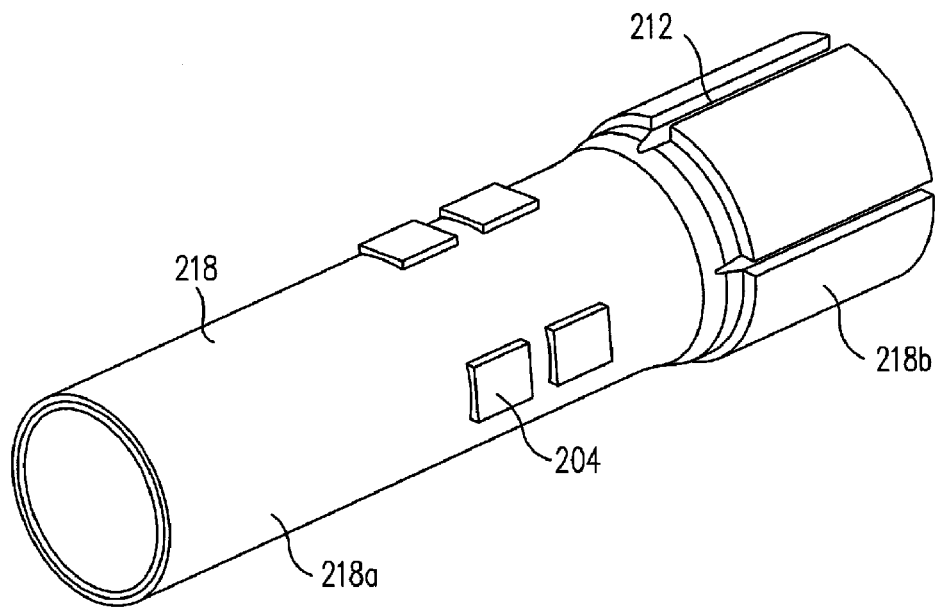
FIG. 4A is a perspective view of an inner tube of a modular force sensor apparatus in accordance with another embodiment of the present invention.

FIG. 4A is a perspective view of an inner tube 218 of modular force sensor apparatus 200 in accordance with an embodiment of the present invention. Inner tube 218 includes a proximal raised end portion 218b and a depressed portion 218a. Strain gauges, as described above with respect to FIGS. 1-3, may be mounted on the surface of depressed portion 218a. Raised end portion 218b may include grooves 112 for routing of wire leads or optic fibers from strain gauges 204.

Figure 4B:
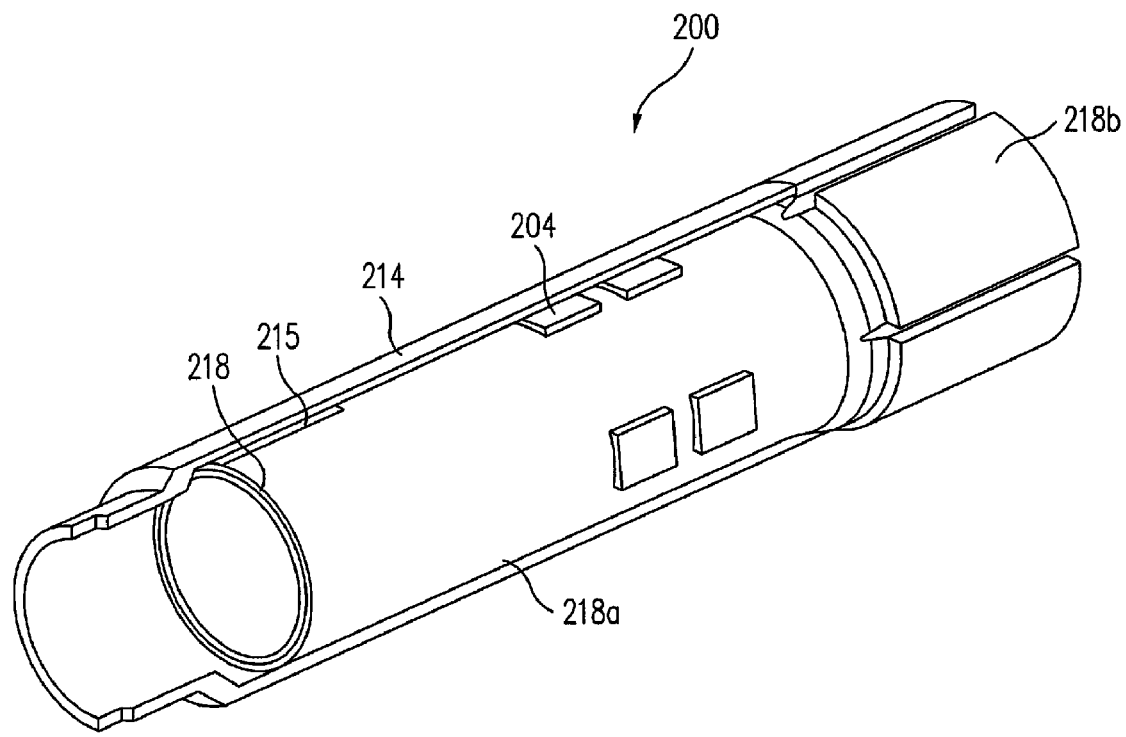
FIG. 4B is a partial cross-sectional view of an outer tube/cover over the inner tube of FIG. 4A of the modular force sensor apparatus in accordance with an embodiment of the present invention.

FIG. 4B is a partial cross-sectional view of an outer tube 214 over the inner tube 218. In one example, outer tube 214 of force sensor apparatus 200 is a concentric tubular structural member made of sufficiently strong materials that can encapsulate the strain gauges and other electronics within an annular gap between the inner and outer tubes 218 and 214. In one embodiment, the concentric tubes are joined rigidly at the proximal end adjacent proximal portion 218b while a narrow annular gap between the distal ends near a distal portion is filled with an elastomeric material 215 that prevents the high and varying axial forces of the wrist and jaw actuator cable or rods from being transmitted through the inner tube carrying the strain gauges. It is noted that the partially isolated tube carrying the gauges may be either the outer or the inner tube. The non-isolated tube of the pair may carry the entire axial cable load. Preferably, the gauges may be placed on the interior tube to isolate the gauges from the environment. In such an embodiment, the outer tube 214 carries the axial cable forces and also permits the outer tube to provide mechanical protection and potentially act as EMI shielding to the gauges 204 on the inner tube 218.

Figure 4C:
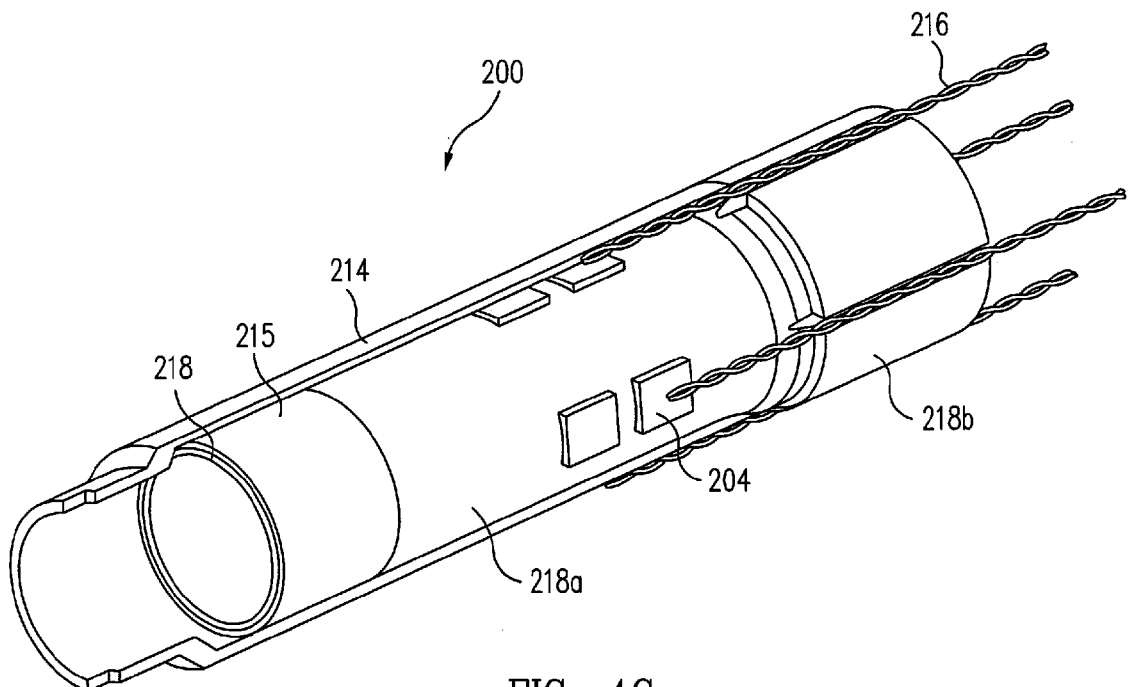
FIG. 4C shows intervening material between the inner and outer tubes of FIG. 4B of the modular force sensor apparatus and wires or fiber optic cables operably coupled to the modular force sensor apparatus in accordance with an embodiment of the present invention.
Figure 4D:
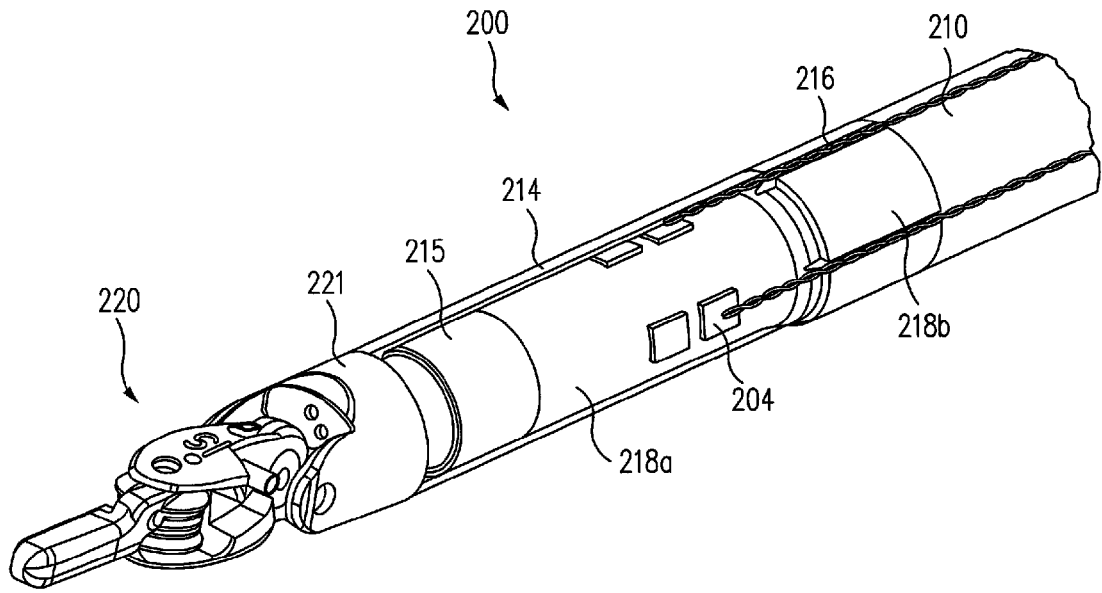
FIG. 4D shows a partial cross-sectional view of the modular force sensor apparatus operably coupled proximal to (or inboard of) a wrist joint of a surgical instrument in accordance with an embodiment of the present invention.

FIG. 4C highlights elastomeric material 215 between the inner tube 218 and outer tube 214 of the modular force sensor apparatus 200, and wires or fiber optic cables 216 operably coupled to gauges 204. FIG. 4D shows a partial cross-sectional view of the modular force sensor apparatus 200 operably coupled proximal to a wrist joint 221 of a surgical instrument in accordance with an embodiment of the present invention. Leads 216 (e.g., shielded twisted pairs, coax, or optic fiber) from the strain gauges 204 may be inlaid into grooves 212 in proximal tube portion 218b of tube 218 and matching grooves in the shaft 210 of a surgical instrument. The leads 216 may then be embedded in an adhesive potting compound such as an epoxy.

In one example, if an outer sensor carrying tube is mounted stationary at the rear mechanism housing, the wire routing may be simplified by not requiring a rotating joint service loop.

Advantageously, the relative shear and compressive properties of elastomers enables this design concept. A suitable elastomer 215 with a low shear modulus permits the relative compression and extension of the cable load carrying tube with respect to the sensor carrying tube (which is connected rigidly at only one end of the tubes as mentioned above). Thus, cable loads and load changes do not affect the sensors. On the other hand, an elastomer confined between two relatively rigid surfaces where the gap between the surfaces is small compared to the extent of the surfaces behaves as a nearly incompressible rigid connection in the direction normal to the confining surfaces, in this case the radial direction of the combined annular tube structure. This causes bending moments carried in the axially loaded tube to be transmitted to and shared by the sensor tube. Thus, the sensor tube can advantageously detect the bending moments due to lateral loads on the instrument wrist and jaws without significant interference or "noise" from the higher varying axial cable loads carried by the other tube. Advantageously, the decoupling of the load carrying members in an endoscopic surgical instrument force sensor enables the separation of undesired jaw actuator tendon forces from desired lateral jaw load induced bending moments on the force sensor.

Alternatively, the desired effect of axially de-constraining the sensor carrying tube from the cable load carrying tube at one end may be obtained by inserting an annular ring of a more rigid low friction material in the annular gap between the unconnected ends of the tubes machined for a very close fit, thereby permitting the relative axial motion but transmitting the lateral motion associated with bending moments due to the lateral tip forces. Another alternative is to make the tubes with a very close fit and apply a low friction coating to one or both surfaces at the distal end. However, these alternatives may create a small deadband in sensor response depending on how close a fit may be reliably obtained. The expansion thermal coefficients of the inner and outer tubes must also be matched or the required close fit may bind when heated or cooled.

It should also be understood that the same decoupling effect achieved with concentric tubes as described above may potentially be achieved with alternating axial finger-like members half (or some number) of which carry the axial cable loads while the alternating (or remaining) ones carry the bending loads. Again, these members may be rigidly connected at the proximal end while they are decoupled in the axial direction at the distal end.

Embodiments described above illustrate but do not limit the invention. It should also be understood that numerous modifications and variations are possible in accordance with the principles of the present invention. For example, the number of strain gauges and their configuration may vary but must allow for applicable force and torque determinations. Accordingly, the scope of the invention is defined only by the following claims.

We claim:

1. A modular force sensor apparatus, comprising:
  a tube comprising a proximal tube portion, a distal tube portion, and a third tube portion that extends between said proximal tube portion and said distal tube portion, wherein said proximal tube portion is configured to operably couple to a shaft of a surgical instrument, wherein said distal tube portion is configured to support mounting a wrist joint of said surgical instrument to a distal end of said tube, and said wrist joint is coupled to an end portion of said surgical instrument, and
  wherein said third tube portion comprises a plurality of strain gauges; and
  a cover over the plurality of strain gauges;
    wherein when mounted on said surgical instrument shaft, said modular force sensor apparatus is positioned at a distal part of said surgical instrument.

2. The apparatus of claim 1, wherein the third tube portion is depressed relative to the proximal tube portion.

3. The apparatus of claim 1, wherein the third tube portion comprises a material different from a material of the shaft of the surgical instrument.

4. The apparatus of claim 1, wherein the plurality of strain gauges includes eight strain gauges in two groups of four, with each of the strain gauges in a group being spaced apart by 90 degrees around the third tube portion.

5. The apparatus of claim 1, wherein the plurality of strain gauges includes six strain gauges in two groups of three, with each of the strain gauges in a group being spaced apart by 120 degrees around the third tube portion.

6. The apparatus of claim 1, wherein the plurality of strain gauges includes four strain gauges spaced apart by 90 degrees around the third tube portion.

7. The apparatus of claim 1, wherein the plurality of strain gauges includes three strain gauges spaced apart by 120 degrees around the third tube portion.

8. The apparatus of claim 1, wherein each strain gauge is aligned with one other strain gauge along an axis parallel to a lengthwise axis of the third tube portion.

9. The apparatus of claim 1, wherein the primary strain sensing direction of each of the strain gauges is oriented parallel to the third tube portion lengthwise axis.

10. The apparatus of claim 1, wherein the plurality of strain gauges is selected from the group consisting of fiber optic, foil, surface acoustic wave, and semiconductor type strain gauges.

11. The apparatus of claim 1, wherein a strain gauge is selected from the group consisting of a Fabry-Perot strain gauge and a fiber Bragg grating strain gauge.

12. The apparatus of claim 1, wherein the cover is comprised of material selected from the group consisting of fiberglass, a resin, and electrical shielding.

13. The apparatus of claim 1, wherein the proximal tube portion includes a plurality of grooves aligned with the lengthwise axis of the third tube portion.

14. The apparatus of claim 1, wherein the wrist joint shares a common pivot axis for yaw and grip axes.

15. The apparatus of claim 1, wherein the end portion of said surgical instrument is selected from the group consisting of jaws, scissors, graspers, needle holders, micro-dissectors, staple appliers, tackers, suction irrigation tools, clip appliers, cutting blades, cautery probes, irrigators, catheters, and suction orifices.

16. A modular force sensor apparatus, comprising:
  an inner tube including:
    a tube portion having a plurality of strain gauges,
    a proximal tube portion for operably coupling to a shaft of a surgical instrument of a robotic surgical system, and
    a distal tube portion; and
  an outer tube covering the inner tube,
    wherein the outer tube is fixedly coupled to the proximal tube portion,
    wherein the outer tube is configured for mounting a wrist joint of said surgical instrument to a distal end of said outer tube, wherein said wrist joint is coupled to an end portion of said surgical instrument so that when said modular force sensor is mounted on the shaft of said surgical instrument, said modular force sensor apparatus is positioned at a distal part of said surgical instrument, and wherein the outer tube is operably coupled to said distal tube portion of the inner tube so that said plurality of strain gauges senses lateral loads substantially without interfering axial loads from the outer tube.

17. The apparatus of claim 16, wherein the outer tube is operably coupled to the distal tube portion via an elastomer.

18. The apparatus of claim 16, wherein the outer tube is operably coupled to the distal tube portion via an annular ring comprising a low-friction material.

19. The apparatus of claim 16, wherein the outer tube is operably coupled to the distal tube portion via a low-friction coating.

20. The apparatus of claim 16, wherein the tube portion is comprised of a material different from the material of the shaft of the surgical instrument.

21. The apparatus of claim 16, wherein the plurality of strain gauges includes eight strain gauges in two groups of four, with each of the strain gauges in a group being spaced apart by 90 degrees around the tube portion.

22. The apparatus of claim 16, wherein the plurality of strain gauges includes six strain gauges in two groups of three, with each of the strain gauges in a group being spaced apart by 120 degrees around the tube portion.

23. The apparatus of claim 16, wherein the plurality of strain gauges includes four strain gauges spaced apart by 90 degrees around the tube portion.

24. The apparatus of claim 16, wherein the plurality of strain gauges includes three strain gauges spaced apart by 120 degrees around the tube portion.

25. The apparatus of claim 16, wherein the plurality of strain gauges is selected from the group consisting of fiber optic, foil, surface acoustic wave, and semiconductor type strain gauges.

26. The apparatus of claim 16, wherein a strain gauge is selected from the group consisting of a Fabry-Perot strain gauge and a fiber Bragg grating strain gauge.

27. The apparatus of claim 16, wherein the outer tube is comprised of a material selected from the group consisting of fiberglass, a resin, and electrical shielding.

28. The apparatus of claim 16, wherein the end portion of said surgical instrument is selected from the group consisting of jaws, scissors, graspers, needle holders, micro-dissectors, staple appliers, tackers, suction irrigation tools, clip appliers, cutting blades, cautery probes, irrigators, catheters, and suction orifices.

29. The apparatus of claim 16, wherein the proximal tube portion includes a plurality of grooves aligned with the lengthwise axis of the tube portion.

\* \* \* \* \*